(12) United States Patent
Ortiz et al.

(10) Patent No.: US 9,339,328 B2
(45) Date of Patent: May 17, 2016

(54) MULTI-ELECTRODE ENERGY DELIVERY DEVICE AND METHOD OF USING THE SAME

(75) Inventors: Mark Ortiz, San Jose, CA (US); Robert Pearson, San Jose, CA (US); Wesley Chung Joe, Fremont, CA (US)

(73) Assignee: AngioDynamics, Inc., Latham, NY (US)

( * ) Notice: Subject to any disclaimer, the term of this patent is extended or adjusted under 35 U.S.C. 154(b) by 776 days.

(21) Appl. No.: 13/390,313

(22) PCT Filed: Aug. 20, 2010

(86) PCT No.: PCT/US2010/046202
§ 371 (c)(1),
(2), (4) Date: Feb. 13, 2012

(87) PCT Pub. No.: WO2011/022674
PCT Pub. Date: Feb. 24, 2011

(65) Prior Publication Data
US 2012/0150172 A1    Jun. 14, 2012

Related U.S. Application Data

(60) Provisional application No. 61/235,494, filed on Aug. 20, 2009.

(51) Int. Cl.
*A61B 18/14* (2006.01)
*A61B 18/00* (2006.01)

(52) U.S. Cl.
CPC .......... *A61B 18/1477* (2013.01); *A61B 18/148* (2013.01); *A61B 2018/00083* (2013.01); *A61B 2018/00196* (2013.01); *A61B 2018/00613* (2013.01); *A61B 2018/00767* (2013.01); *A61B 2018/00875* (2013.01); *A61B 2018/143* (2013.01); *A61B 2018/1432* (2013.01);

(Continued)

(58) Field of Classification Search
CPC .................................................. A61B 18/1477
See application file for complete search history.

(56) References Cited

U.S. PATENT DOCUMENTS 6,235,023 B1 *  5/2001  Lee et al. ........................ 606/41
6,610,054 B1 *  8/2003  Edwards et al. ................ 606/41

(Continued)

FOREIGN PATENT DOCUMENTS

WO       0174252 A2    10/2001
WO    2004082498 A1     9/2004

OTHER PUBLICATIONS

PCT International Search Report for PCT/US2010/046202 mailed May 27, 2011.

(Continued)

*Primary Examiner* — Michael Kahelin
(74) *Attorney, Agent, or Firm* — Zachery F. Madonna (57) ABSTRACT

An energy delivery device for treating a patient includes a probe body and a plurality of elongate electrode elements that extend radially away from the probe body when deployed into tissue of the patient. The electrode elements are adapted to receive electrical treatment energy such as irreversible electroporation (IRE) pulses from an energy source. In one embodiment, each electrode element has a longitudinally varying electrical resistance at the electrode-tissue interface along the electrode so as to provide a uniform electric field along the length of the electrode. The uniform electric field allows a more uniform ablation of tissue within a treatment zone.

5 Claims, 10 Drawing Sheets

(52) U.S. Cl.
CPC . *A61B2018/1467* (2013.01); *A61B 2018/1475* (2013.01)

(56) References Cited

U.S. PATENT DOCUMENTS

2001/0001819 A1  5/2001  Lee et al.
2002/0022864 A1  2/2002  Mahvi et al.
2004/0087939 A1  5/2004  Eggers et al.
2006/0293731 A1  12/2006  Rubinsky et al.
2009/0036958 A1  2/2009  Mehta

OTHER PUBLICATIONS

Supplementary European Search Report for EP10810679 dated Feb. 6, 2013.

* cited by examiner

SECTION B-B

FIG. 6A

SECTION A-A

MULTI-ELECTRODE ENERGY DELIVERY DEVICE AND METHOD OF USING THE SAME

CROSS REFERENCE TO RELATED APPLICATIONS

This application is a national phase of PCT application No. PCT/US2010/046202, filed Aug. 20, 2010, which claims priority under 35 U.S.C. 119(e) to U.S. Provisional Application No. 61/235,494, filed Aug. 20, 2009, all of which are incorporated herein by reference.

FIELD OF THE INVENTION

The present invention relates to medical devices. More specifically, the present invention relates to a multi-electrode energy delivery device for delivering electrical energy to treat a patient.

BACKGROUND OF THE INVENTION

Antenna needles can be placed within or in proximity to a tumor or other undesired tissue mass and RF energy applied between the two needles. The RF energy causes ionic agitation in the tissues surrounding the antenna and results in resistive heating of the targeted tissue as the RF energy travels from the active antennae toward the negatively charged grounding antennae. Multiple needle probes require a minimum of two insertion sites. When the probes are placed in a non-parallel relationship to each other along the active antennas, the energy dispersion will be unequal along the length of the probes, with greater heating occurring proximally (closer to the physician) and less heating occurring between the most distal portions (closer to the patient). Unequal energy dispersion can lead to incomplete treatments and possible system failures as electrical resistance dips below or above an acceptable level.

SUMMARY OF THE DISCLOSURE

Various configurations of antennae as well as electrode probes for ablation of undesired tissue in a patient are known in the art. The term "antennae" and "tines" are known in the art as referring to aspects of radiofrequency (RF) devices and the term "electrode" is known in the art as referring to electrical devices in the context of electroporation (RE) devices and especially in irreversible electroporation (IRE) devices. For convenience and efficiency, in this application, the terms "antennae", "tine" and "electrode" are used interchangeably whether in single or plural form to refer to parts that deliver electrical energy in RF as well as RE and IRE devices.

A detailed explanation of IRE can be found, for example, in U.S. Patent Application Publication Number 2006/0293731, entitled "Methods and systems for treating tumors using electroporation", application Ser. No. 11/165,961 filed on Jun. 24, 2005, which is hereby incorporated by reference. In IRE, electrical pulses in the range of microseconds to milliseconds can be applied to a target tissue zone to produce defects in the cell membrane that are nanoscale in size. The defects in the cell membrane lead to a disruption of homeostasis and eventually cause the cells to die. IRE devices can be designed to be non-thermal and the IRE pulses do not destroy connective and scaffolding structure in the target zone such as nerves and blood vessels.

The IRE pulses are applied using electrical probes, which can be monopolar, bipolar or multi-electrode. The probe designs are similar to the RF probes and accordingly are subject to some of the same problems involving energy distribution along the electrodes. Specifically, the electrical resistance along the length of a pair of electrodes in a multi-electrode probe varies because the electrodes are not in a parallel arrangement. In the pair of electrodes, the resistance at the electrode-tissue interface is the lowest near the proximal end and is the highest at the distal end due to varied spacing between the electrodes. This results in a varying electrical field strength along the electrodes which may cause incomplete treatment or system malfunction if resistance falls outside acceptable limits as determined by the hardware or software constraints.

A single bipolar probe or multi-electrode probe can be used to ablate diseased or unwanted tissue. The positive and negative electrodes are located on a single probe and the tissue is ablated as energy flows from the positive to the negative electrode. Although the bipolar design provides efficient energy deposition in the tissue, the maximum ablation volume is limited and the resulting cylindrical shape of ablation often does not correspond with the targeted tumor shape.

Electrode arrays with an umbrella-like profile achieves larger, more spherical ablations with a single puncture. In this type of probe, two or more outwardly curving tines (electrodes) are placed within the tumor and RF energy flows from each active tine or electrode in the array towards a grounding pad on the patient's skin. Although the array design allows for larger ablations with a single device and single puncture site, the energy dispersion is less efficient than bipolar designs because of the greater distance between the positive electrodes and negative ground pad.

When the array is deployed, the distance between the two electrodes is not parallel but instead varies along the electrode length, with the distance between electrodes being the greatest at the distal ends. The energy flow will be the highest at a point which represents the shortest distance between the tines, and this flow will decrease at points where the distance between the electrodes increases. This uneven energy flow pattern can lead to incomplete treatment at the periphery of the targeted tissue volume and overheating or electrical current overload at the proximal section of the active tines.

The current device and method equalizes the energy emission along the lengths of the electrodes. In one aspect, an energy delivery device for treating a patient includes a probe body and a plurality of elongate electrode elements that extend radially away from the probe body when deployed into tissue of the patient. The electrode elements are adapted to receive electrical treatment energy such as irreversible electroporation (IRE) pulses from an energy source. In another aspect of the invention, each electrode element has a longitudinally varying electrical resistance at the electrode-tissue interface along the electrode so as to provide a uniform electric field along the length of the electrode. The uniform electric field allows a more uniform ablation of tissue within a treatment zone.

In one aspect, variable resistance is accomplished by the use of a resistive element which compensates for the variation in energy emission. Specifically, the resistor/resistive element can be designed to balance energy emission by several methods including but not limited to varying the thickness of the resistor along the active electrode length, creating a pattern of holes or "defects" in the resistor element or using a resistor element with varying dielectric strength. The resistive element may also be an intrinsic component of the electrode itself such as a metallic oxide layer that may readily be grown or formed to a controlled thickness with appropriate heat processing or via anodizing. Using the device and method disclosed herein, the resistance encountered at any electrode-tissue interface point between two electrodes can be maintained at the same level regardless of the varying distance between electrodes due to the geometry of the deployed probe or non-parallel spacing during placement within the targeted tissue.

BRIEF DESCRIPTION OF THE DRAWINGS

A more complete understanding of the present device and method can be derived by referring to the detailed description when considered in connection with the following illustrative figures. In the figures, like reference numbers refer to like elements or acts throughout the figures. Throughout the specification, the term "distal" is consistently used in reference to the device or portion of the device farthest from the user and "proximal" refers to the end closest to the user of the device.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the current device and method. It will be understood, however, by those skilled in the relevant arts, that the present device and method can be practiced without these specific details. In other instances, known structures and devices are shown or discussed more generally in order to avoid obscuring the present device and method. In many cases, a description of the operation is sufficient to enable one to implement the various forms of the device and method. It should be noted that there are many different and alternative configurations, devices and technologies to which the disclosed device and method can be applied. The full scope of the device and method is not limited to the examples that are described below.

For purpose of this application, the term resistance and impedance have the same meaning and are used interchangeably.

Figure 1:
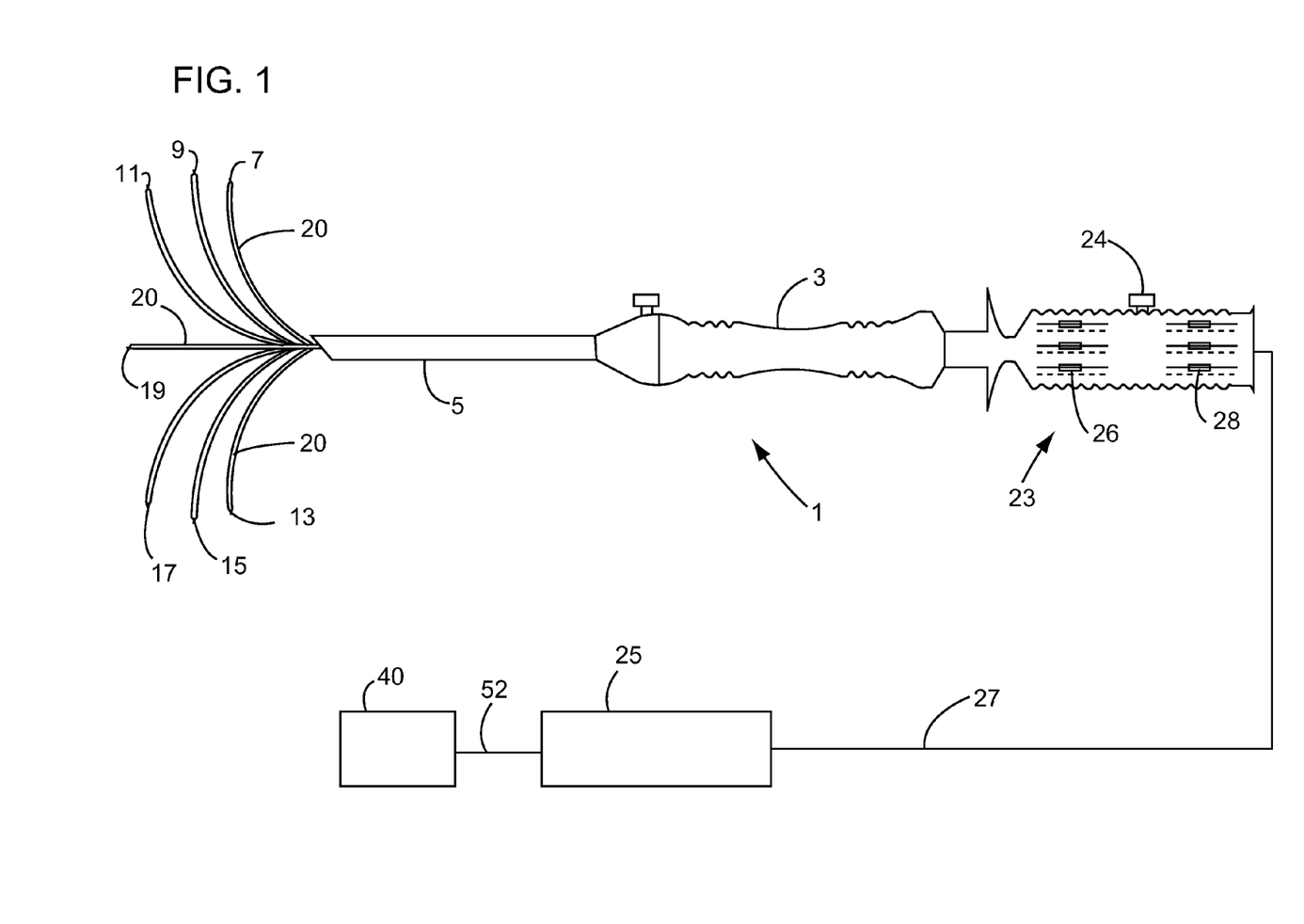
FIG. 1 illustrates a medical treatment system including an energy delivery device with electrodes in a deployed position.

FIG. 1 illustrates a medical treatment system including an energy delivery device 1 with electrodes in a deployed position. The energy delivery device 1 is designed for tissue treatment using electrical treatment signals (i.e., electrical energy such as electrical pulses for general or specific purposes, for electrical, electroporative or radiofrequency purposes). The energy delivery device 1 includes a main handle 3, an elongated probe portion 5 having a sharp distal end for piercing tissue and a plurality of curved antenna or electrodes 7,9,11,13,15,17 and center electrode 19. The energy delivery device is designed as a single stick device in which the sharp distal end of the probe portion 5 pierces tissue so as to position the device 1 inside the tissue. The electrodes 7-19 are then deployed through the end of the probe portion 5.

Proximal handle 23 is advanced towards or retracted from the proximal end of the main handle 3 to respectively deploy and retract the electrodes 7-19 from the distal end of the elongated probe portion 5. In the embodiment shown, the proximal handle 23 has been fully advanced towards the proximal end of the main handle 3 so as to show the electrodes in their fully deployed position. The energy delivery device 1 includes a deployment mechanism (inside the handle 23) configured to independently control the extent (length) of the deployment of each electrode from the distal end of the probe 5 using electrode slide tabs 26. Each slide tab 26 controls a corresponding electrode movement independently of other electrodes. As shown in FIG. 1, there are seven slide tabs 26.

The resistor sleeves 20 are disposed over and around the electrodes 7-19 to provide variable resistance at the electrode-tissue interface as will be discussed in more detail later herein. Each electrode in combination with an associated resistor sleeve 20 comprise an electrode element. A main slide tab 24 controls the longitudinal sliding of all sleeves 20 over the electrodes 7-19 at the same time. The energy delivery device 1 includes a deployment mechanism (inside the handle 23) configured to independently control the longitudinal movement of each sleeve 20 relative to the corresponding electrode using resistor slide tabs 28. Each slide tab 28 controls a corresponding resistor movement. As shown in FIG. 1, there are seven resistor slide tabs 28.

The energy delivery device 1 is designed to apply IRE pulses to treat a patient. For example, the device 1 is designed to generate a n sets of m pulses per set with each pulse having a duration of 1 microsecond to 1 millisecond, where n and m=2-20 and the pulse voltage being in the range of 400 volts/cm and 2500 volts/cm.

As shown, the energy delivery device 1 is configured to apply 9 sets of 10 pulses with each pulse having a pulse duration of 50-150 microseconds and the voltage being 1000 volts/cm to 2000 volts/cm depending on the tissue type being treated. This is more fully described in applicant's application entitled "System and Method for Interactively Planning and Controlling a Treatment of a Patient with a Medical Treatment Device", Ser. No. 12/751,854, filed Mar. 31, 2010, which is incorporated herein in its entirety by reference.

The energy delivery device 1 is coupled to an energy source (e.g., electrical pulse generator) 25 via a cable 27 or other attachment mechanisms known in the art. A user computer 40 is connected to the pulse generator 25 through a communication link 52 and controls the energy source to treat a patient. The cable 27 contains insulated wires that are coupled to the respective electrodes 7-19. The energy source 25 can be capable of releasing energy for purposes of electroporation (including irreversible electroporation) radiofrequency, or other applications. This device can be utilized in applying direct current (DC) or alternating (AC) electrical signals that act on one or more cellular structures including but not limited to internal or external membranes, layers, bi-layers, mitochondria, the nucleus cellular structures within the nucleus, ribosomes DNA, RNA, reticulum, lysosomes, tubules vacuoles as well as application to structures such as proteins and lipids therein.

Figure 2:
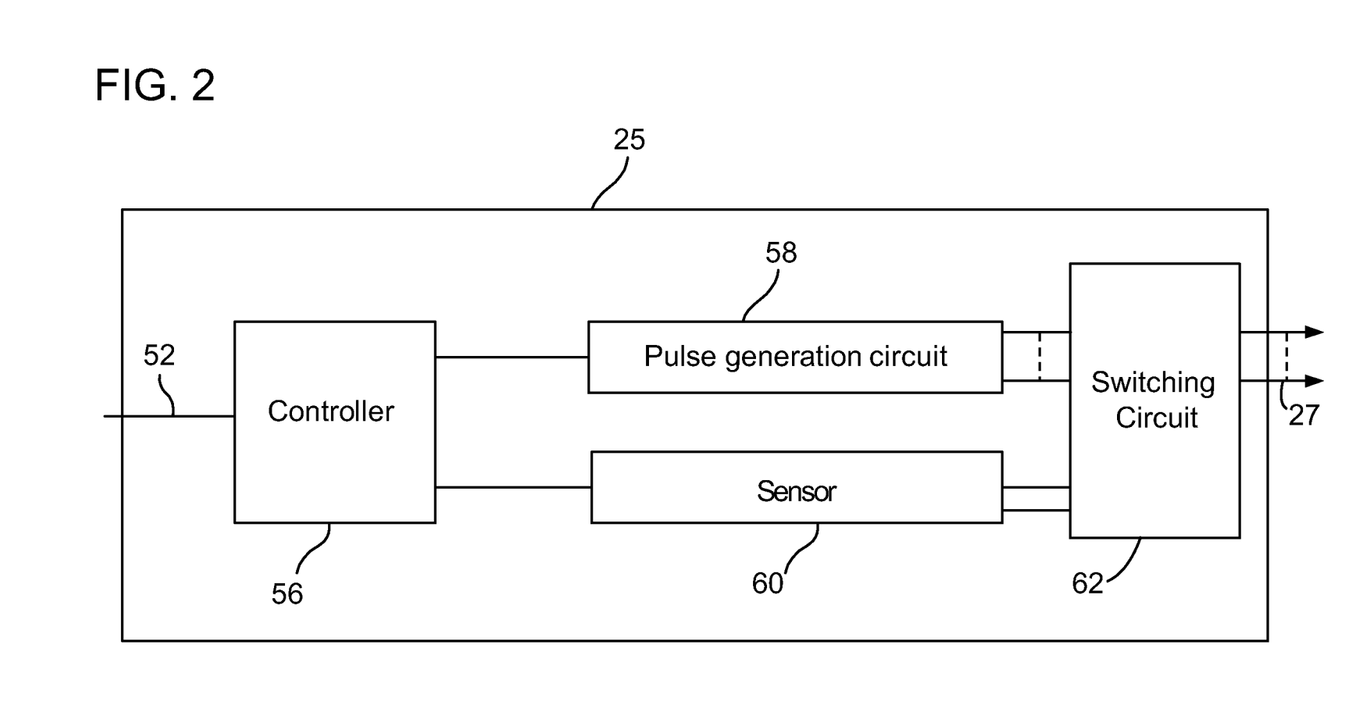
FIG. 2 illustrates a functional block diagram of a pulse generator.

FIG. 2 illustrates a functional block diagram of the pulse generator 25 according to one aspect of the device. A USB (universal serial bus) connection 52 carries instructions from a user computer 40 to a controller 56. The controller 56 can be a computer similar to the computer 40 as shown in FIG. 1. The controller 56 can include a processor, ASIC (application-specific integrated circuit), microcontroller or wired logic. The controller 56 sends the instructions from the user computer 40 to a pulse generation circuit 58. The pulse generation circuit 58 generates the pulses and transmits them to the electrodes 7-19 through the cable 27. As shown, the pulses are applied one pair of electrodes at a time, and then switched to another pair. A switching circuit 62 is coupled to the controller 56 and switches the electrode pairs based on the instructions received from the computer 40 through the controller. For example, the switching pattern of the electrode pairs can be 19-7, 19-9, 19-11, 19-13, 19-15, and 19-17.

A sensor 60 can sense the resistance (e.g., current and/or voltage) between each pair of the electrodes in real time and communicate such information to the controller 56, which in turn, communicates the information to the computer 40.

Figure 3:
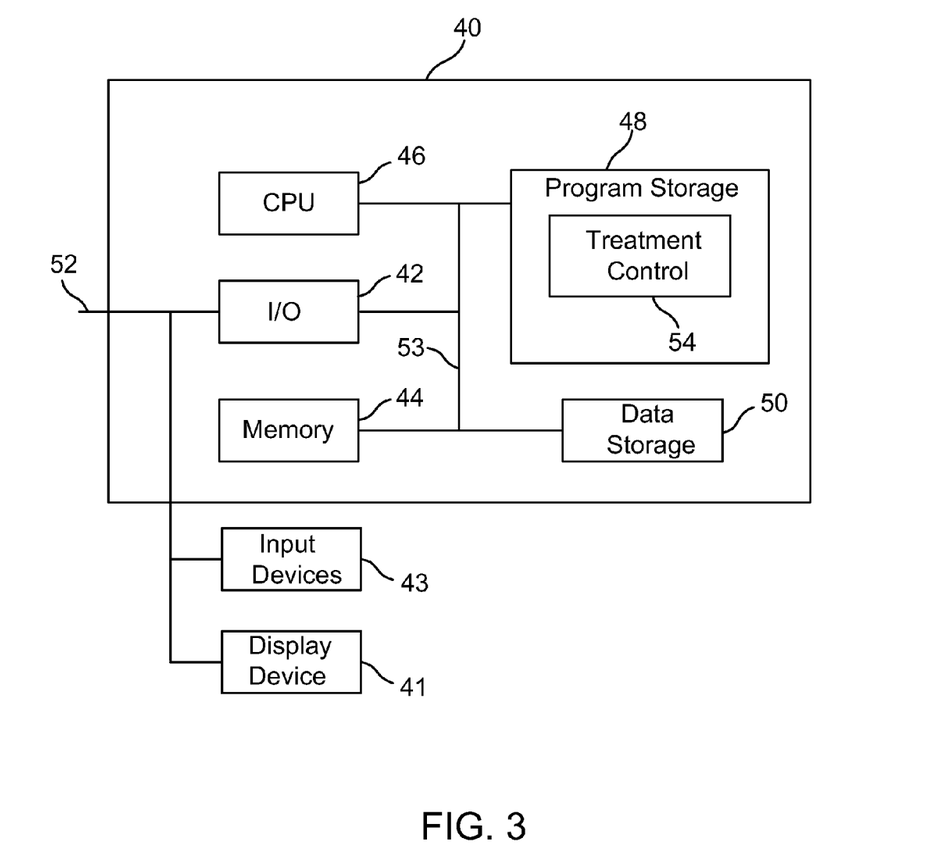
FIG. 3 illustrates a functional block diagram of a user computer for managing treatment for a patient.

Referring now to FIG. 3, the user computer 40 of the present device manages treatment for a patient. The computer 40 is connected to the communication link 52 through an I/O interface 42 such as a USB (universal serial bus) interface, which receives information from and sends information over the communication link 52 to the pulse generator 25. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment control module 54 which includes a user interface module that interacts with the user in planning for, executing and reviewing the result of a treatment. The user interacts with the treatment control module 54 through input devices 43 (e.g., keyboard, mouse, touch screen, trackball and the like) and a display device 41. Any of the software program modules in the program storage 48 and data from the data storage 50 can be transferred to the memory 44 as needed and is executed by the CPU 46.

In one aspect, the computer 40 is built into the voltage generator 25. In another embodiment, the computer 40 is a separate unit which is connected to the voltage generator through the communications link 52. In another aspect, the communication link 52 is a USB link.

Figure 4:
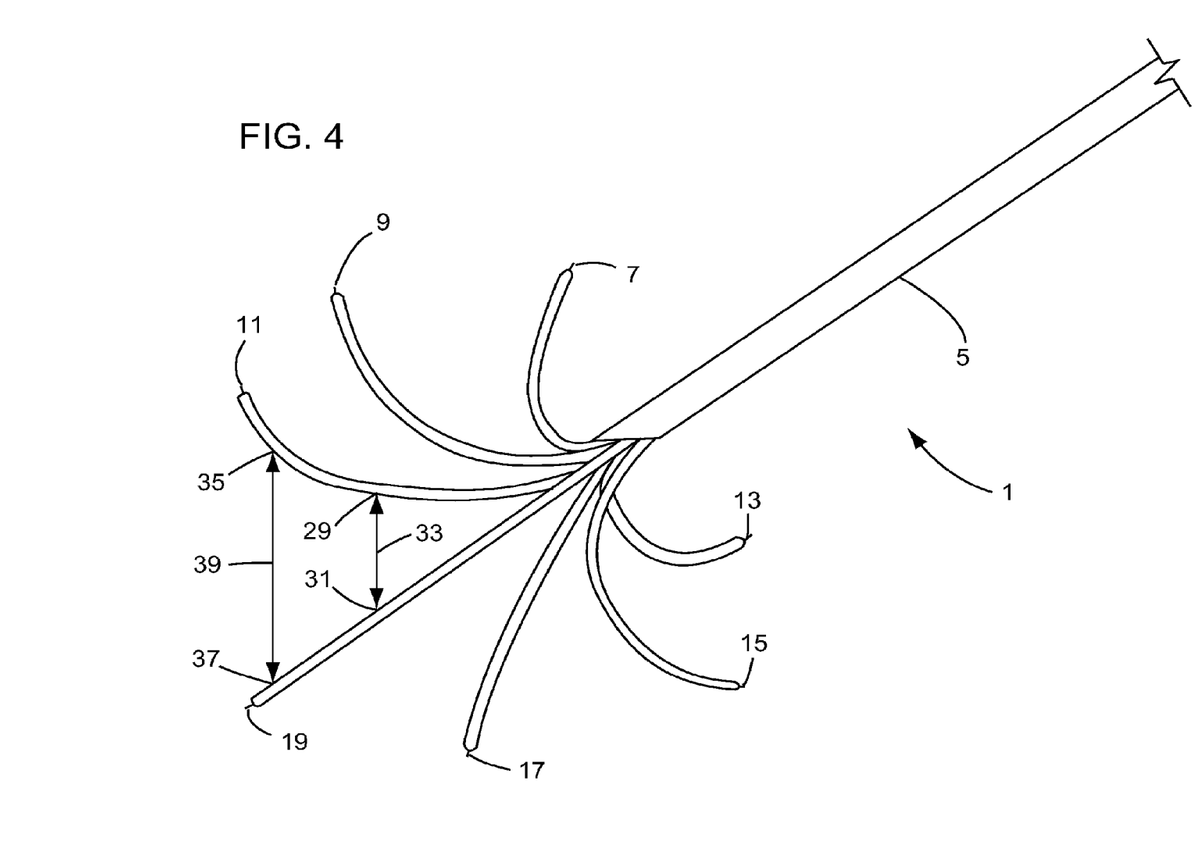
FIG. 4 is an isometric view of the distal portion of the energy delivery device of FIG. 1 illustrating the varying distances between two active electrodes.

FIG. 4 is an isometric view of the distal portion of the energy delivery device of FIG. 1 illustrating the changing distances between electrodes (such as from a point more proximal to elongated portion 5 to a point more distal in relation to elongated portion 5). Shown deployed, electrode 11 curves outwardly away from center electrode 19, which in this aspect of the device is straight. The distance between two respective points on electrodes 11 and 19 that are equidistant from the elongated probe portion 5 is greater on two respective, equidistant points located at the distal end of the electrodes than between two equidistant points located proximally. As an example, the distance 33 between point 29 of electrode 11 and point 31 of electrode 19 (where point 29 and point 31 are each equidistant from the distal portion of the elongated portion 5) is less than the distance 39 between equidistant points (35, 37).

The electrical resistance at the electrode-tissue interface between electrodes 11 and 19 will be different between points 29 and 31 over distance 33 than between points 35 and 37 over distance 39. In general, as the distance between any two probes increases, the electrical strength will decrease. From a clinical perspective, a varying electrical resistance pattern can result in incomplete treatment at the periphery of the tissue volume and also in some cases can result in disruption of energy flow due to the generators response to unacceptably high resistances.

Still referring to FIG. 4, the rate of change of resistance or impedance between such equidistant points along the length of the antennas in some instances is constant such that a mathematical determination can be made of the resistances between any two points. By describing mathematically certain energy changes with a given antenna deployment pattern, a determination can be made as to how to design a resistive element that will equalize the resistance across the electrodes along the entire active length. A ratio can be determined for a proportionality equation where on left side of the equation the numerator is the distance 33 (from here forth also called "D1" which is the distance between points 29 and 31) and the denominator on the left side of the equation is the distance 39 (from here forth also called "D2" which is the distance between points 35 and 37), and on the right side of the equation the numerator is the resistance between points 29 and 31 (here forth called "R1") and the denominator on the right side of the equation is the resistance between the points 35 and 37 (here forth called "R2"). The rate of resistance change can thus be predicted by the equation D1/D2 is proportional to R1/R2. Conceivable variations include those where calculations can be made for points along the antennas or electrodes that are not equidistant or even two points along one antenna, or where averages of resistances are used in calculations (or a combination of these).

Once the rate of resistance or impedance change has been determined a resistive element can be designed to alter the resistance at any point on the electrodes to achieve homogenous energy dispersion along the entire length of the active electrodes. The resistive element can be comprised of a non-conductive material that prevents or impedes the flow of current or RF energy such as a polymer, metallic oxide or polyester. The resistive element can be applied to the electrodes using numerous methods and techniques known in the art such as heat shrinking a tubular structure over the body, dipping, anodizing, coating, heat-processing, spraying or otherwise applying the resistive element.

Figure 5:
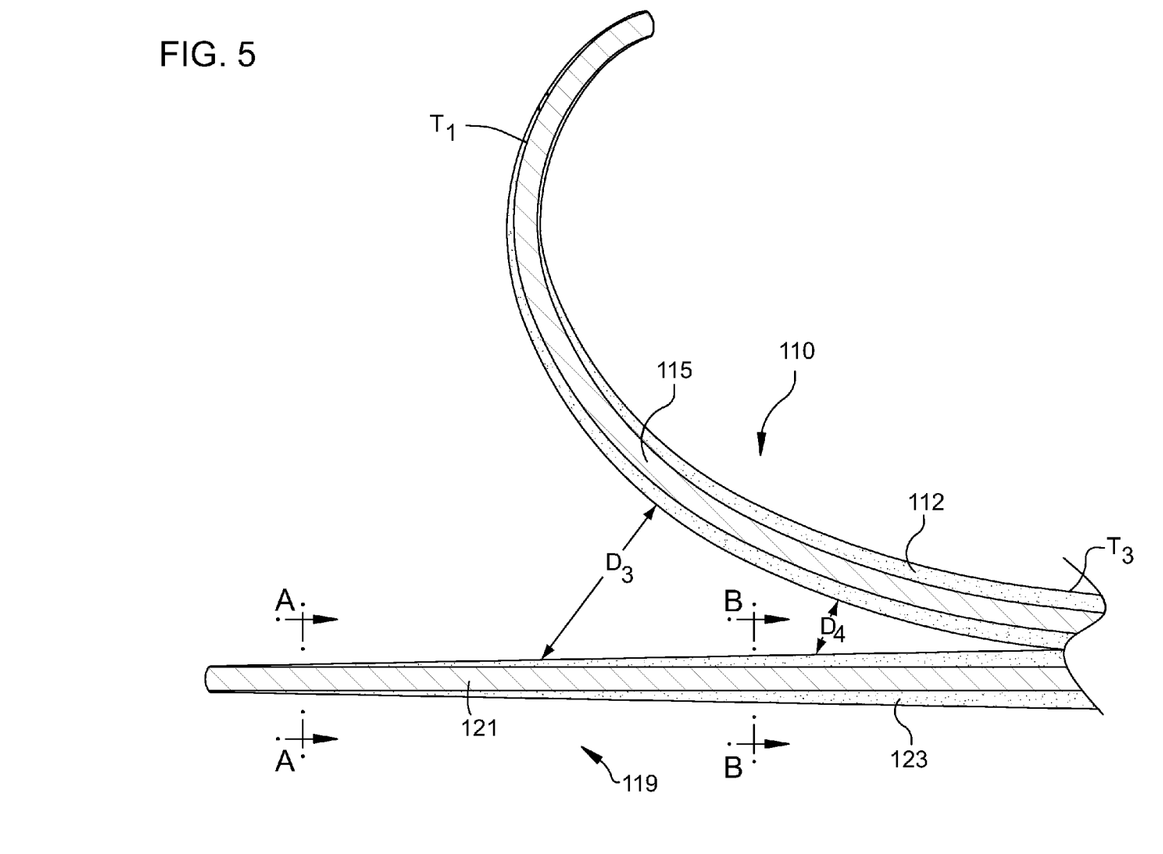
FIG. 5 is an enlarged cross-sectional view of two electrodes illustrating resistive elements of various thicknesses along the active electrode length.

FIG. 5 illustrates one aspect of a resistor (resistive element) coaxially surrounding the deployed electrodes for the energy delivery device 1. Enlarged distal portions of two electrode elements 110 and 119 are shown in cross-section. Resistive element 112 coaxially surrounds electrode 115. Resistive element 123 coaxially surrounds electrode 121. The resistive elements 112 and 123 function to equalize the effective resistance or impedance between the two electrodes along the length of the electrodes. For example, two points on electrode elements 110 and 119, respectively, each equidistant from the distal end of each electrode are farther apart from each other than is the distance between two equidistant points located at a relatively more proximal point of the antennae; Distance D3 is greater than distance D4. Therefore the resistance at the two described points over D4 is different than between equidistant points at D3. By varying the thickness of resistive element 112 from a maximum thickness T3 to a minimum thickness T1, the effective resistance can be equalized between location D4 and D3 as well as along the entire length of the active electrodes. An additional approach of mathematically describing the equalization of resistances between two points on separate antennas equidistant from the shaft distal end would be to state that the resistance due to a first distance D4 plus the resistance change created by resistive elements of each antenna equals the resistance due to a second distance D3 plus the resistance change created by resistive element thickness at points over D3. Also shown for completeness are lines A-A and B-B showing relatively distal (A-A) and proximal (B-B) lines for cross-sections of electrode 119 that are depicted respectively in FIGS. 6A and 6B.

Figure 6A:
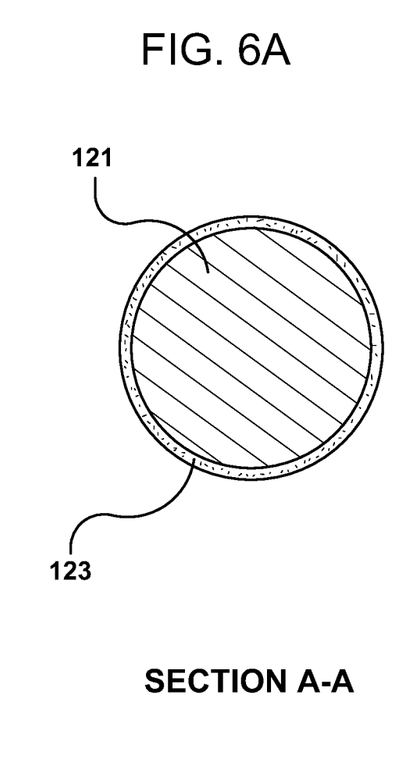
FIGS. 6A-6B illustrate a cross-sectional view of the central electrode from FIG. 5 along A-A which is distal, meaning closest to the patient, and along B-B which is more proximal along the electrode.
Figure 6B:
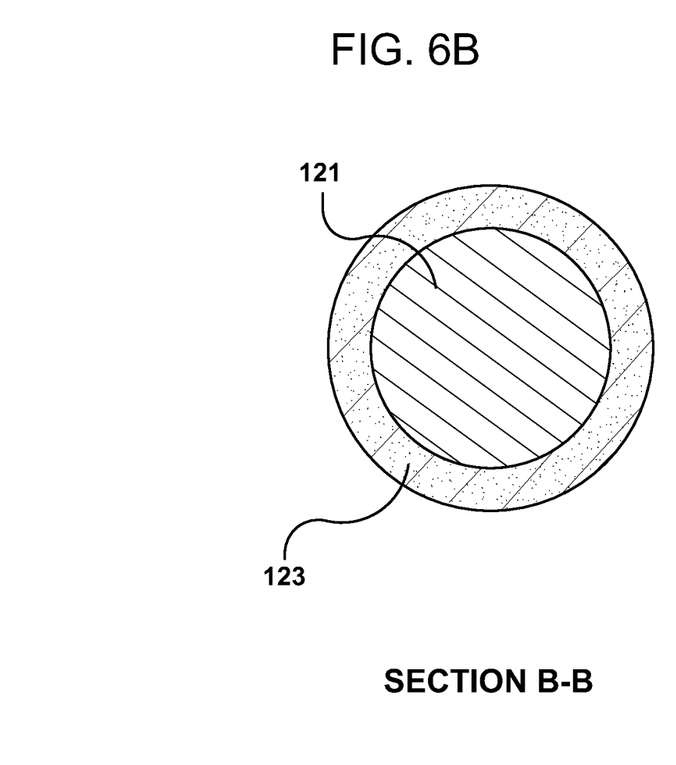

FIGS. 6A and 6B depict cross-sections of electrode 119 taken along lines A-A and B-B respectively of FIG. 5 and illustrate the differing thickness of resistive element 123 along the length of the electrode body 121. At line A-A, the thickness of resistive element 123 is much less than the thickness of resistive element 123 at line B-B. Accordingly, the natural resistance created in the region of B-B relative to A-A will be equalized by the varied thickness (and varied resistance) of the non-conductive barrier of the resistive element 123.

Figure 7A:
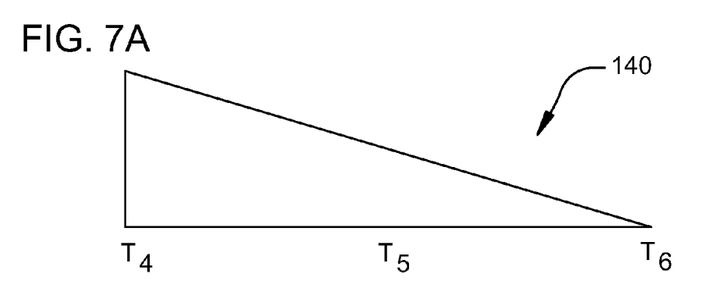
FIGS. 7A-C illustrate three different transition patterns of the resistive elements.
Figure 7B:
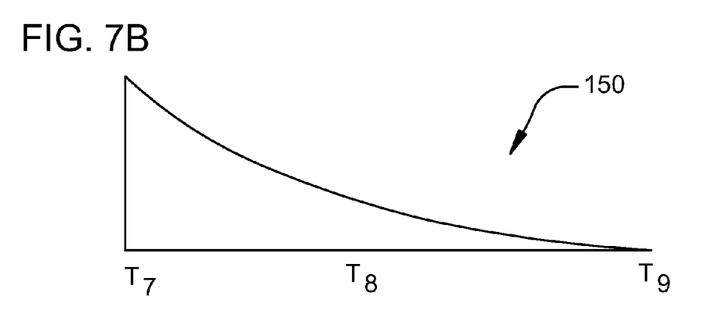
Figure 7C:
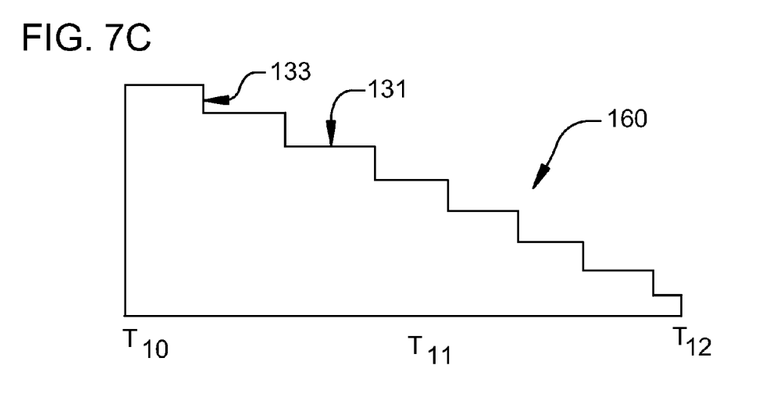

Resistive patterns can be formulated based on mathematical determinations of distances between electrodes and resistances for points along the lengths of separate electrodes, and these calculations can be made for various patterns of electrode number and display. FIGS. 7A-C illustrate three different resistive patterns for balancing resistance based on probe type, in which the Y-axis represents the thickness of the resistor element (therefore, representing effective resistance at the electrode-tissue interface) and the X-axis represents the position on an electrode in a distal direction. FIG. 7A represents resistive design 140 based on a linear mathematical relationship applicable to straight, non-curved "V" shaped antenna groups in which the resistance continuously varies along the electrode in a linear manner. The resistive element is thickest at T4 (proximal point), thinner at T5 (midpoint), and thinnest at T6 (distal point) to account for natural resistance imbalances. FIG. 7B illustrates resistive design 150 based on a non-linear distance relationship between two electrodes in which the resistance continuously varies along the electrode in a non-linear manner. This design would be applicable to curved or umbrella shaped arrays. Specific thickness values are calculated using non-linear mathematical equations. In resistive design 150, the resistive element is thickest at T7 (proximal point), thinner at T8 (midpoint), and thinnest at T9 (distal point). FIG. 7C illustrates a step-wise design 160 which can be either linear or non-linear depending on the geometry of the probe. It is easier to manufacture the resistive element of the step-wise design than an element that is continually changing in thickness along its entire length. The design 160 thickness is greatest at T10 (proximal point), thinner at T11 (midpoint), and thinnest at T12 (distal point). The step-wise pattern can be seen specifically in comparing the thickness at 133 with the thinner layer at 131.

One method of manufacturing a stepwise variable thickness resistor sleeve is to apply resistive coating in uniform layers. For example, if each layer is applied in 20 micron thickness, then the first step would be 20 microns, followed by a second 20 micron layer over the first layer to make a 40 micron layer, followed by a third 20 micron layer to make a 60 micron layer, and so on. Likewise, if the resistive layer is actually made up of separate tubes, then stacking tubes with increasing diameters can also provide a stepped variable thickness (somewhat like a telescoping atenna).

For any bipolar electrode design there is a geometrical relationship between the spacing of the electrodes. This relationship can be described with theoretical or empirical data. A few examples are as follows: the electrodes can be aligned parallel to each other with a fixed distance between electrodes so that the separation distance can be described as D (the distance between two electrodes at a desired determination point along the electrodes) equals a constant. In other variations, electrodes can be substantially straight but not parallel to each other, and would have a relationship of the linear equation known in the art of $y=m \, x+b$ where y is a point on a line relating to the y-coordinates of a graph, m is the slope of the line, x is the point on a line relating to the x-coordinate on a graph, and (b) is the y-intercept.

A version of the $y=m \, x+b$ equation can be applied to two substantially straight, nonparallel electrodes; where the distance between two electrodes at a desired determination point along the electrodes is (D) and where one electrode is substantially straight and represents the x-axis, while the second electrode represents a substantially straight line on an x-y graph. In that case the same equation ($y=m \, x-b$) can be rewritten as $D=a*X+b$. In that case (D) is the distance between electrodes at the desired determination point along the electrodes, (a) is the slope of separation, X is a point along the electrode that is substantially straight and represents the x-axis, and (b) is the initial distance between the two electrodes at the point where electrodes exit from the elongated portion.

In yet other aspects, the electrodes are curved and electrodes have relationships that are a function of the type of curvature. Many types of curvature exist specifically, in simple radial deployment of electrodes such that the separation distance can be described by the following equation, describing electrodes that curve out from the elongated probe portion away from each other when moving from the distal end of the elongated probe to the distal end of an electrode: $D=2*R \sin \theta$, where D is the distance between electrodes, R is the radius of a hypothetical circle created by an electrode if it were extended to the extent of making a circle, and θ (theta) is the angle created between two straight lines drawn, each starting at the point that is the center of the circle; with one line extending vertically to a first point on an electrode immediately as it exits the distal end of the elongated portion when held at a horizontal position, and the second line extending from the point that is the center of the circle to a second point on the same electrode located more distally (closer to the patient) along the electrode and corresponding with the point at which a vertical distance determination is being made between two electrodes.

Many other deployments could be developed and some could be three-dimensional in nature so it would require more complicated math to describe the separation distance. It is even possible to develop complicated multi-segmented arrays that are best described with empirical reference tables. Various aspects include resistance varying linearly with separation distance requiring resistor addition or removal using a geometrically linear method to equalize measured resistance. It is also possible to have a step wise linear approximation so that several distinct electrodes or areas of resistor approximately compensate for the separation distance.

Figure 8:
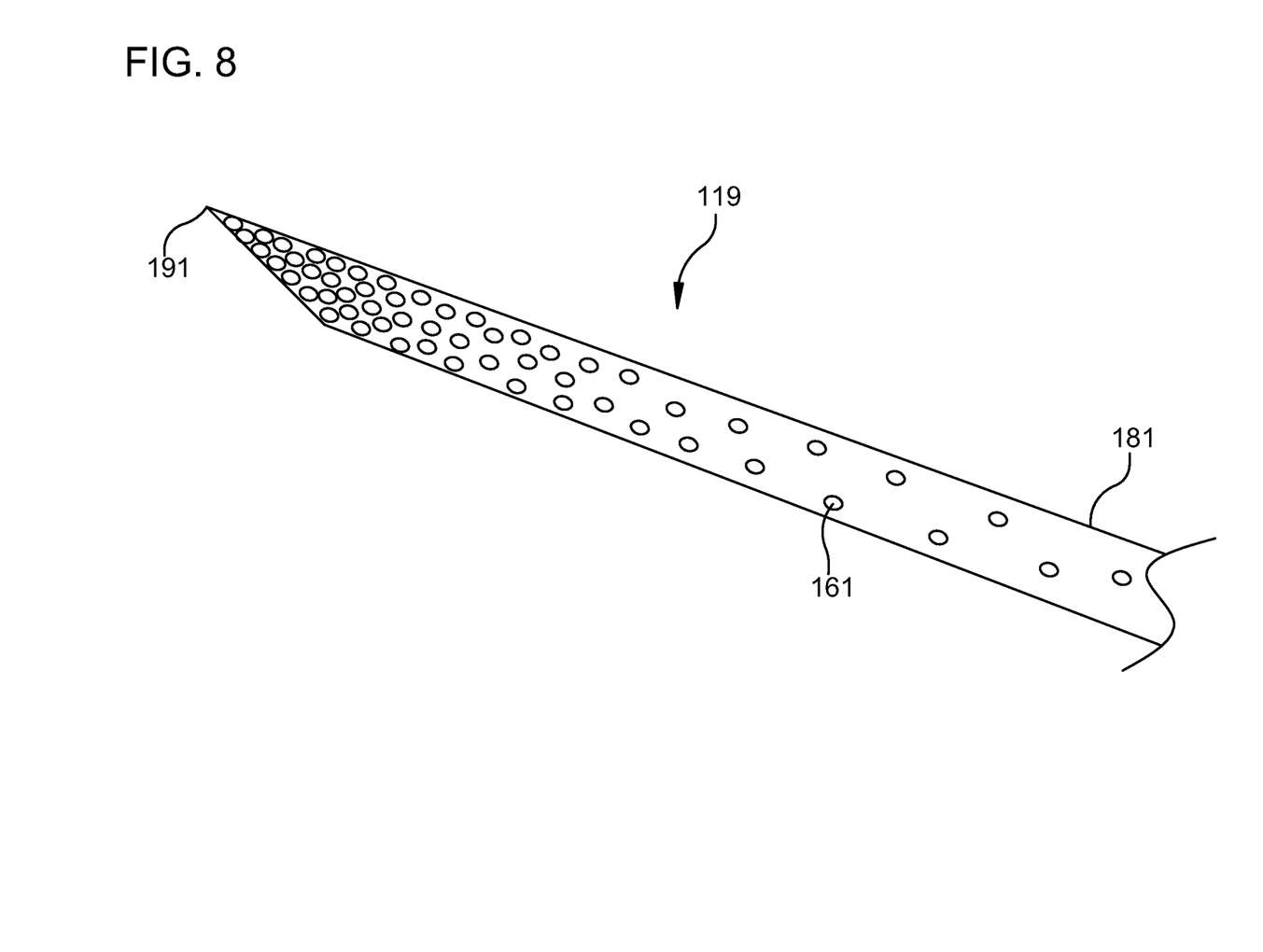
FIG. 8 depicts a partial electrode with a resistive element wherein the resistive element comprises a series of holes which vary in number along the length of the electrode.

Another method of balancing resistance or impedance along the electrode is by providing a resistive element that includes a series of holes forming a pattern that selectively alters the resistance. FIG. 8 shows an enlarged view of the distal portion of an electrode 119 with a resistive element 20 (such as, in certain aspects, metallic oxide or insulation layer known as Kapton™ from DuPont Corporation on the exterior that is a material with holes placed in the material). The resistive element 20 includes a series of holes 161 arranged in a pre-determined pattern. As depicted in FIG. 8, the resistance can be altered by holes 161 of equal size throughout the length of the antenna but with a variable hole density (number of holes per surface area) along the length. As shown, the hole density increases in the distal direction to provide a lower resistance towards the tip. Though the size of the holes depicted in FIG. 8 is the same throughout the length of the electrode, it is possible to change the resistance by having holes of varying size throughout the length of the electrode. In another aspect, the hole density and hole size can both be altered so long as the resistance at the electrode-tissue interface along the electrode decreases in the distal direction. In certain aspects the total area of removed resistor due to holes at a given cross-section of the antenna is made different than the total area removed at a separate cross-sectional point, and in certain other aspects the rate of change of the area removed through holes is constant along the length in either a distal or proximal direction. Electrical energy (such as for radiofrequency, reversible electroporation, irreversible electroporation, or superporation) will flow relatively more freely through the non-insulated portions of the antenna as defined by the series of holes 161. In the embodiment shown, the hole pattern becomes denser as it approaches the distal end 191 of electrode 119 to provide an increasing density (exposed electrode area density) along the electrode and thereby provide a continuously decreasing resistance (continuously increasing electrode conductivity) at the electrode-tissue interface along the electrode. The holes can be completely absent at the proximal section 181 where the antenna in an array are closest together. By applying the resistive coating with more holes placed distally, the resistance between any two equidistant points can be altered to achieve an overall uniform energy dispersion between the entire active length of corresponding antennae.

The indentations, holes, or defects in the resistive element can be made via laser, mechanical, cutting, punching, chemical etching, mechanical etching, piercing, electrical, heating, cooling, release of gas or fluid or solid to the material, or other methods known in the art. The thickened coating can be added in various shapes such as circles, squares, triangles, or in constant or partial layers, or be in a pattern such as a spiral along the antenna. In certain aspects the resistance at any point along the antennas or along the coatings can be changed within the addition of a gel or plastic material that is separate from or made a part of the antenna or coating through applications such as the use of heat. In certain aspects the coatings are made of materials that are more dense than, less dense than, or of equal density as the antennas. In certain aspects the coatings utilize pockets of air or other gas, liquid, or gel to alter the resistance at points along the antennas.

In another aspect, variable resistance along the electrodes can be achieved by changing the conductivity of the electrodes themselves. One way is to change the surface profile of the electrodes. For example, the distal portion of each electrode can have a rougher profile than the proximal portion so that there is more effective surface area which is in contact with the tissue at the distal portion. More contact means that there is less electrical resistance at the distal portion where the electrode spacing is further apart. Another way to change the conductivity of the electrodes is to coat the electrodes with a hydrophobic material at the proximal portion and hydrophilic material at the distal portion to provide the same tissue-electrode surface resistance profile along the electrodes. Still another way to change the conductivity of the electrodes is to infuse a more conductive material in the distal direction such that the effective surface area in contact with the tissue increases in the distal direction which reduces the resistance and increases conductivity in the distal direction.

Figure 9:
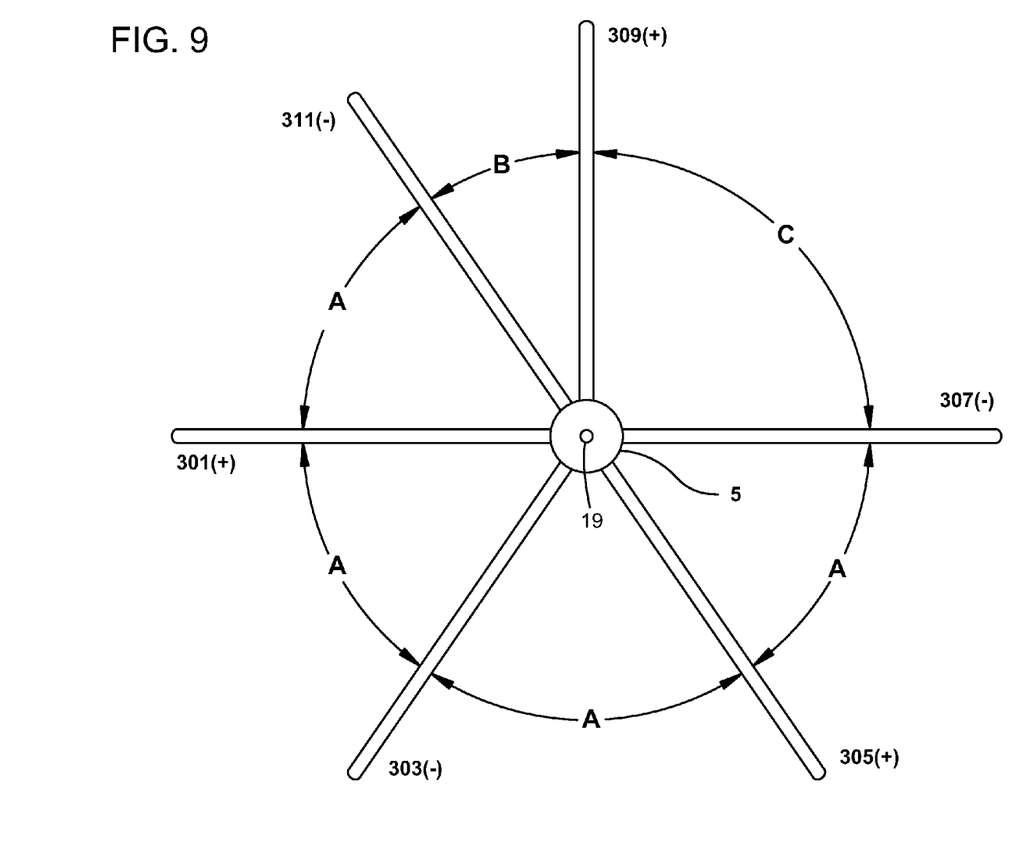
FIG. 9 is an end view of a deployed electrode array illustrating misalignment between two electrodes.

In yet another aspect, the resistive element such as those shown in FIGS. 5-8 can be longitudinally slidable relative to the electrode. Conventionally, slidable resistive sleeves are used to adjust the active electrode lengths. However, the resistive sleeve of the current invention is capable not only of adjusting the active electrode length but also of altering the resistance and altering the impedance along the length of the electrode. Referring to the schematic of FIG. 9, an end view of a multi-polar electrode array, similar to FIG. 4, is shown in a deployed position. Individual electrodes 301, 303, 305, 307, 309 and 311 extend radially outward from probe shaft 5 into the target tissue. In one embodiment, electrodes 301, 305 and 309 are of a positive polarity as indicated by the (+) sign. Electrodes 303, 307 and 311 are of a negative polarity as indicated by the (−). When connected to a generator, energy (for general or specific purposes, for electrical, electroporative, or radiofrequency purposes) will flow from the positive electrodes to negative electrodes, creating a spherical ablation volume. The flow of energy will be impacted by the relative position of two adjacent electrodes. If during deployment, any of the electrodes becomes misaligned, resistance or impedance of the energy flow between those misaligned electrodes will be altered. As an example, the relative spacing between electrodes in FIG. 9 is shown as a uniform distance A for distances between each electrode except for distance related to electrode 309. Electrode 309 is misaligned as indicated by the non-uniform distance C between electrode 307 and 309 as well as the non-uniform distance B between electrode 309 and 311. The spacing between electrodes 309 and 311 is closer than desired. As a result, the impedance or resistance between electrodes 307 and 309 will be higher than the resistance or impedance between electrodes 309 and 311. This means that more energy would be applied between electrodes 309 and 311, than between electrodes 307 and 309 which may result in incomplete treatment of the target tissue and shorting out of electrodes. This difference can be compensated for by the current invention under the control of the treatment control module 54 as will be explained in more detail below.

The device of the current invention with its slidable, variable thickness resistive sleeve can be used to compensate for misalignment between electrodes after the device has been deployed within the target tissue. For electrodes 311 and 309 which are too close together, the resistive sleeve of each electrode can be slid distally (away from the user) along the electrode body. This action in certain aspects will cause a decreased overall conductivity between the two electrodes (or between parts of the electrodes) as the thicker resistor is advanced distally. Conversely, electrodes 309 and 307 are spaced too far apart resulting in below acceptable levels of energy transfer between the positive electrode 309 and negative electrode 307. To alter the resistance or impedance between these two electrodes, the slidable resistive sleeve is slid proximally (toward the user) which in certain aspects will allow a greater amount of energy to flow between the electrodes (or between parts of the electrodes). In this manner, the medical practitioner can individually compensate for misaligned electrodes without having to retract, reposition and redeploy the entire device.

Figure 10:
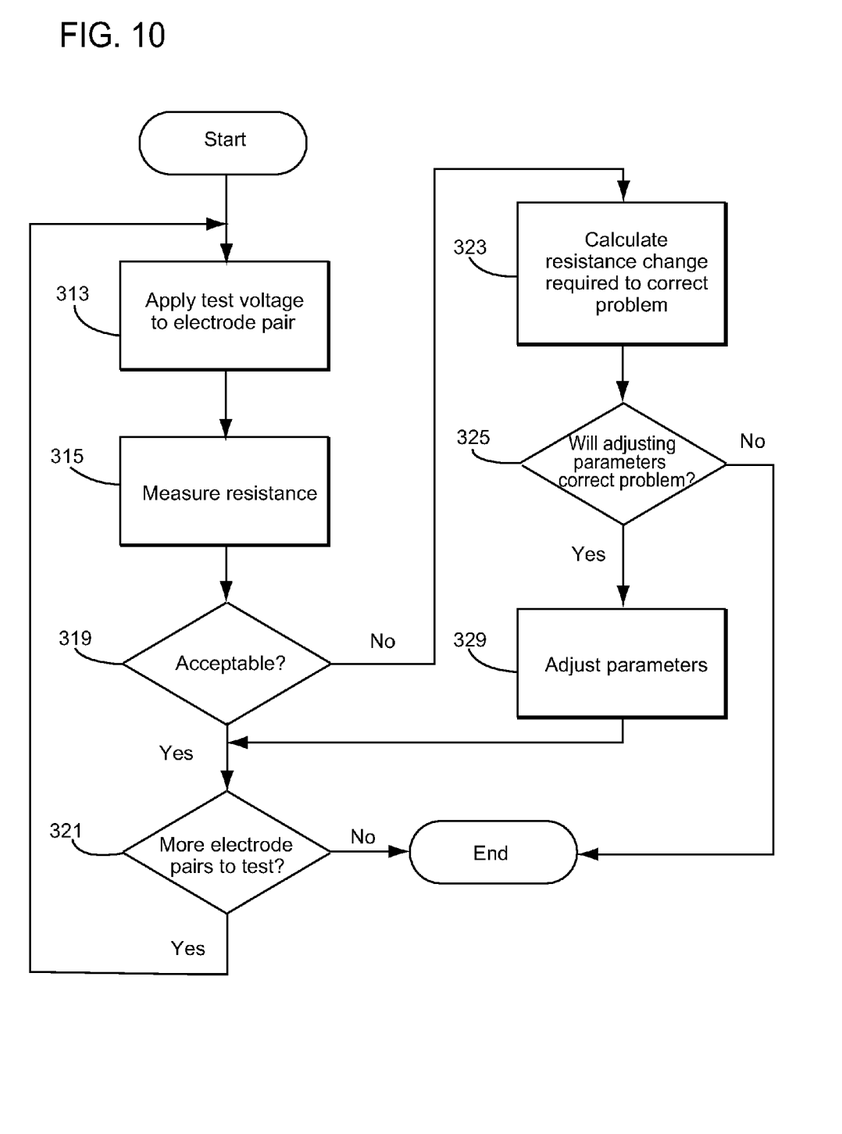
FIG. 10 is a flowchart illustrating the steps of pre-testing the deployed electrode and adjusting a slidable resistor element based on the results of the pre-test.

In a further aspect, the treatment control module 54 can be configured to determine not only the real part, but also the imaginary part of the resistance/impedance from each antenna/electrode and identifying a misaligned antennae or antennas. The treatment control module 54 can also be configured to calculate necessary adjustments required to achieve acceptable energy flow and re-align the resistive element to achieve the desired level of energy flow. FIG. 10 illustrates one flow chart of the steps executed by the treatment control module 54 prior to the start of the treatment procedure.

Prior to the execution of steps in FIG. 10, certain procedures are performed. Specifically, the physician identifies a target tissue zone to be ablated in a patient and selects an appropriate multi-electrode probe for the treatment (e.g., probe with 5 electrodes). Then, the selected probe is inserted into the identified tissue zone by piercing the tissue with the sharp end of the probe portion 5. Once the probe portion 5 is inserted, the physician deploys the electrodes by pushing the proximal handle 23 towards the proximal end of the main handle 3. The steps of FIG. 10 are then executed.

In step 313, a test signal (e.g., test pulse/voltage) is sent through the cable 27 to a selected set or pair of deployed electrodes which are positioned inside the tissue area to be treated. In one aspect of treating tissue using IRE, this test pulse is approximately $1/10$ to $1/5$ the maximum treatment voltage but no lower than 200 volts and no higher than 500 volts. (It should be noted that in a preferred embodiment for IRE treatment, valid treatment voltages are between 500 to 3000 volts.) As shown, one or more test pulses of 400 volts is used for each pair of electrodes.

Resistance (either only the real part, imaginary part or both) from the test pulses can be determined by the sensor 60 (e.g., a current sensor) in step 315 and passed to the treatment control module 54 through the controller 56. In decision 319, the control module 54 compares the determined resistance against acceptable operating values using standard or proprietary software interfaces and database. If the resistance is determined to be acceptable (e.g., in a range of 2000 Ohms and 50 Ohms), then decision 321 asks whether there are more electrode pairs to be tested. If yes, then the control module 54 goes back to step 313 to repeat the test signal for the remaining pairs. If not, the routine ends.

Referring back to decision 319, if the resistance is determined to be unacceptable (e.g., outside the range of 2000 Ohms and 50 Ohms), then control passes to step 323. Step 323 determines adjustments in one or more pulse delivery parameters that are necessary to correct the problem. The pulse delivery parameters include voltage, duration and number of treatment signals, electrode extensions, resistor extensions and resistance/impedance matching among others. In decision 325, the control module determines whether the adjustments can be made to bring the resistance to an acceptable level given the physical limits of the system such as maximum voltage and resistance. If not, the control module 54 advises the physician to reinsert the device 1 through the display device 41 and the routine ends. If the adjustments can be made, then step 329 adjusts the pulse delivery parameters as determined in step 323. In one aspect, the control module 54 calculates the recommended direction and length of the adjustment of the resistor sleeves 20 or electrodes. A GUI software interface, which is a part of the control module 54, can display the recommended adjustments for the physician to make manual adjustments to the identified electrodes or alternatively, a driver mechanism inside the proximal handle 23 can automatically retract or advance the resistive element 20 or an electrode by the recommended distance.

In one aspect, the treatment control module 54 is designed to detect whether the electrodes are deployed at different depths. This may occur, for example, if a bodily structure such as a bone has obstructed the full deployment of an electrode. If so, assuming that adjustments can be made to bring the resistance to an acceptable level as determined in step 325, the control module 54 determines the adjustment of the pulse delivery parameters. This may include instructions to the physician to manually withdraw and redeploy one electrode using the electrode slide tab 26, and to move the electrode slide tab 26 and/or resistor slide tab 28 to particular positions, among others. This process can be repeated for each set of misaligned electrodes.

Once the adjustments have been completed, the physician can start the treatment procedure. Under the control of the treatment control module 54, the pulse generation circuit 58 and the switching circuit 62 will apply a series of electrical treatment signals (e.g., IRE pulses) through the deployed electrodes according to a predetermined switching pattern. Because each electrode has a longitudinally varying electrical resistance at the electrode-tissue interface along the length of the electrode, a more uniform electric field along the electrodes is established which results in a more uniform and complete treatment of the tissue zone.

In certain embodiments the coating is a nonconductive coating. In certain cases, circular indentations have been created in a coating placed on the antennae. In another aspect, indentations in the coating have been created by laser treatment of a coating prior to placement on the antennae or antennas; the coating has circular indentations placed such that the proximal portion of the antennae (farthest from the patient) has the smallest number of indentations, and the distal end (closest to the patient) has the greatest number of circular indentations, and the rate of increase in hole number changes at a constant rate as one travels proximal to distal along the antenna toward the trocar tip. In certain aspects, the rate of change in hole number is not constant along the antenna length. In other cases, the object of the coating is to account for the fact the antenna are deployed in a nonlinear pattern and without the coating, in that particular embodiment, the resistance is lowest and current highest at the most proximal portion of the antenna. In certain aspects the coating has been placed on the exterior of one or more antenna through one or more of sliding, adhering, melting, melding, spraying, painting, or in other ways known to the art for coupling the coating with the antenna. In certain aspects the circular indentations are made deep enough to create holes where no coating exists within the boundaries of the circles.

In yet other aspects the indentations are shown as a pattern where the number of indentations in the coating increases, with a definite, constant rate of increase, such that the most indentations are at the most distal end of the antenna, closest to the patient indentations can be placed on an angle (in relation to a theoretical, horizontal line placed through the antenna and where the horizontal line cross-sects the antenna at a 90 degree angle from the direction the antenna move toward when deployed). The angle of the pattern can be in any position that can be used to alter the resistance within the antenna; the indentations or holes can be placed at any point along the length of the antennae or at any point along the length of the coating, and indentations or holes can be of one or a combination of shapes or one or more of a combination of sizes for a combination of sizes and shapes). In various aspects the indentations, holes, or other defects in the coating are placed on part of one antennae, on one whole antennae, or on one or more of several antennas.

Relating to the material or coating, a pulsed Nd:YAG laser (or one or its harmonic wavelengths 1064 nm 532 nm, 355 nm, or 266 nm) can be used to make holes or patterns in Kapton™ insulation from DuPont Corporation or its equivalent. In certain aspects lasers, products or materials from the company Quantronix (East Setauket, N.Y.) are utilized. Any laser capable of creating defects in coatings known in the art can be utilized for this purpose. In other aspects the coating is altered using a laser including one or more type of laser including but not limited to gas, chemical, dye, metal-vapor, solid-state, semiconductor, free electron, gas dynamic. Raman, or Nuclear pump laser.

The indentations, impressions, holes, cuts, notches, deep recesses, or other defect or effect to alter resistance in the coating or coatings are each of a diameter or length on the scale of at least one of a centimeter, millimeter, micrometer, nanometer, picometer femtometer, as well as an attometer. In certain aspects the depths or diameter of one or more indentations varies from one or more other depth or indentation. In other aspects holes and indentations are both utilized, and in certain embodiments at least one of indentations as well as holes are utilized with added materials on one or more devices. In yet other aspects different antennas of the same device (or different sections of a single antennae) have different patterns of at least one of indentations, holes, as well as added material. Alternatively, there is one layer or coating with different patterns or rates of change of pattern of indentations, holes, or added materials.

The indentations and layers or coatings added to one, several, or part of one antennae (that includes one or more of solids, liquids, or gels that can be used to alter resistance) are each of a thickness or length on the scale of at least one of a centimeter, millimeter, micrometer, nanometer, picometer, femtometer, as well as an attometer. In one aspect the thickness of a least one coating is between 1 and 100 micrometers. For specific embodiments the thermal index of at least one coating used is between 200 and 220° C. In other aspects at least one coating used has a thermal index that is between 0° C. and 400° C.

In other aspects, more than one coating is added to at least one antennae with varying densities or a coating is added to at least one antennae or a section of antennae where at least one of the coating density, thickness, or layer number vary along the length of the antennae. In further aspects solids or gels are utilized together as coatings and with various densities and thicknesses. In other aspects the individual defects or holes are filled with liquids, solids, or gels of one or varying densities.

The apparatus and method disclosed herein can be used in laparoscopic, percutaneous, natural orifice procedures (NOTES), as well as open surgical procedures as well as when the target tissue either actually is one of the following tissues or is within the following tissues: digestive, skeletal, muscular, nervous, endocrine, circulatory, reproductive, integumentary, lymphatic, urinary, and soft tissue. The method can be used to target tissue of or within a vessel, a liver, or lung tissue. The method can also be used singly or in combination in tissues that are in the pancreas, prostate, uterus, and brain. The method can also be used to target singly or in combination tissues that are benign, malignant, cancerous, neoplastic, preneoplastic, or tumorous.

The apparatus and method disclosed herein can be used with various treatment modalities including radiofrequency, reversible electroporation, irreversible electroporation, and superporation.

The above disclosure is intended to be illustrative and not exhaustive. This description will suggest many modifications, variations, and alternatives may be made by ordinary skill in this art without departing from the scope of the device and method. Those familiar with the art may recognize other equivalents to the specific embodiments described herein. Accordingly, the scope of the device and method described herein is not limited to the foregoing specification.

What is claimed is:

1. An energy delivery device for treating a patient with irreversible electroporation (IRE) comprising:
    a probe body;
    a plurality of elongate electrodes extending radially away from the probe body when deployed into tissue of the patient, and adapted to receive IRE pulses from a pulse generator; and
    a plurality of variable resistors with each variable resistor being disposed over an associated elongate electrode, each variable resistor adapted to provide a continuously longitudinally varying electrical resistance along the each variable resistor.

2. The energy delivery device of claim 1, wherein the each variable resistor surrounds the associated elongate electrode and the thickness of the each variable resistor decreases in a distal direction so as to provide a lower electrical resistance in the distal direction.

3. The energy delivery device of claim 1, further comprising a center electrode extending longitudinally along a longitudinal axis of the probe body, wherein the each variable resistor surrounds the associate elongate electrode and the thickness decreases in a distal direction so as to provide a lower electrical resistance in the distal direction.

4. The energy delivery device of claim 1, further comprising:
    a processor;
    a treatment control module executable by the processor and adapted to determine a resistance between a pair of the elongate electrodes and determine an adjustment parameter for at least one of the pair of electrodes based on the determined resistance.

5. The energy delivery device of claim 4, wherein the treatment control module is adapted to determine the voltage of the IRE pulse to be delivered as the adjustment parameter.

* * * * *